United States Patent [19]

Shibahara et al.

[11] Patent Number: 4,497,811
[45] Date of Patent: Feb. 5, 1985

[54] 1-OXADETHIACEPHALOSPORIN COMPOUND AND ANTIBACTERIAL AGENT CONTAINING THE SAME

[76] Inventors: Seiji Shibahara, No. 3-18-30, Tsukushino, Machida-shi, Tokyo; Tsuneo Okonogi, No. 2-5-11-403, Susukino, Midori-ku, Yokohama-shi, Kanagawa; Yasushi Murai, No. 2-37-19, Futaba, Yokosuka-shi, Kanagawa; Shunzo Futkatsu, No. 1-13, Ichigayata-machi, Shinjika-ku, Tokyo; Taro Niida, No. 127, Nakakibougaoka, Asahi-ku, Yokohama-shi, Kanagawa; Tadashi Wakazawa, No. 2602-53, Kamariya-cho, Kanazawa-ku, Yokohama-shi, Kanagawa, all of Japan

[21] Appl. No.: 510,132
[22] Filed: Jul. 1, 1983

[51] Int. Cl.$^3$ .................. C07D 498/04; A61K 31/535
[52] U.S. Cl. ..................................... 514/231; 544/90; 544/92; 260/245.3; 514/232
[58] Field of Search ................. 260/245.3; 544/92, 90; 424/248.51, 248.54, 248.56

[56] References Cited

U.S. PATENT DOCUMENTS 4,258,041  3/1981  O'Callaghan et al. .............. 424/246

Primary Examiner—Robert T. Bond
Attorney, Agent, or Firm—Thomas E. Arther; Raymond M. Speer

[57] ABSTRACT

New 1-Oxadethiacephalosporins having a 3-loweralkyl thio group, and antibacterial compositions containing the same.

2 Claims, No Drawings

1-OXADETHIACEPHALOSPORIN COMPOUND AND ANTIBACTERIAL AGENT CONTAINING THE SAME

DETAILED DESCRIPTION OF THE INVENTION

This invention relates to a new 1-oxadethiacephalosporin compound.

We, the present inventors, have made extensive researches in an attempt to seek for such 1-oxadethiacephalosporin compounds which exhibit a wide range of antibacterial spectrum and which are active against a wide variety of resistant bacteria, and we have now synthesized new 1-oxadethiacephalosporins by introducing different substituents on 1-oxadethiacephalosporin nucleus at 7- and 3-positions thereof. On examination of antibacterial properties of these new compounds, we have found that these new compounds now synthesized have a wide range of antibacterial activities and also exhibit a highly curative effect in therapeutic treatment of bacterial infection even upon oral administration of the new compound, so that we have accomplished this invention.

According to a first aspect of this invention, therefore, there is provided a 1-oxadethiacephalosporin compound of the general formula:

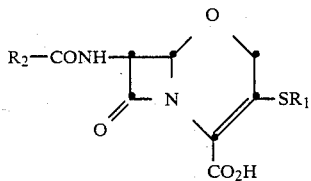
(I)

wherein $R_1$ represents an alkyl group of 1 to 4 carbon atoms and $R_2$ is a group of the formula:

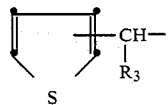

in which $R_3$ is a hydrogen atom or carboxyl group, or a group of the formula:

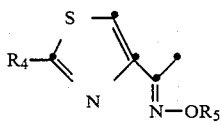

in which $R_4$ is a hydrogen atom or amino group, and $R_5$ represents an alkyl group of 1 to 4 carbon atoms or a group of the formula:

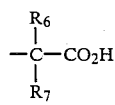

where $R_6$ and $R_7$ may be the same or different and each is a hydrogen atom or an alkyl group of 1 to 4 carbon atoms, or a non-toxic salt or non-toxic ester of said compound.

Typical examples of the compounds of the general formula (I) include the following:

| Example No. | Name of compound |
|---|---|
| 1(b) | 7-(2-thienylacetamido)-1-oxa-1-dethia-3-methylthio-3-cephem-4-carboxylic acid |
| 2(b) | 7-(3-thienylacetamido)-1-oxa-1-dethia-3-methylthio-3-cephem-4-carboxylic acid |
| 3(b) | 7-[2-(2-thienyl)-2-carboxyacetamide]-1-oxa-1-dethia-3-methylthio-3-cephem-4-carboxylic acid |
| 4(b) | 7-[2-(3-thienyl)-2-carboxyacetamido]-1-oxa-1-dethia-3-methylthio-3-cephem-4-carboxylic acid |
| 5(b) | 7-[2-(3-thienyl)-2-phenoxycarbonylacetamido]-1-oxa-1-dethia-3-methylthio-3-cephem-4-carboxylic acid |
| 6(b) | 7-[2-(2-amino-4-thiazolyl)-2-methoxyiminoacetamido]-1-oxa-1-dethia-3-methylthio-3-cephem-4-carboxylic acid trifluoroacetate |
| 7(b) | 7-[2-(2-amino-4-thiazolyl)-2-ethoxyiminoacetamido]-1-oxa-1-dethia-3-methylthio-3-cephem-4-carboxylic acid trifluoroacetate |
| 8(b) | 7-[2-(2-amino-4-thiazolyl)-2-carboxymethoxyiminoacetamido]-1-oxa-1-dethia-3-methylthio-3-cephem-4-carboxylic acid trifluoroacetate |
| 9(b) | 7-[2-(2-amino-4-thiazolyl)-2-phenoxycarbonylmethoxyiminoacetamido]-1-oxa-1-dethia-3-methylthio-3-cephem-4-carboxylic acid trifluoroacetate |
| 10(b) | 7-[2-(2-amino-4-thiazolyl)-2-carboxyprop-2-oxyiminoacetamido]-1-oxa-1-dethia-3-methylthio-3-cephem-4-carboxylic acid trifluoroacetate |
| 11(b) | 7-[2-(2-amino-4-thiazolyl)-2-phenoxycarbonylprop-2-oxyiminoacetamido]-1-oxa-1-dethia-3-methylthio-3-cephem-4-carboxylic acid trifluoroacetate |

Amongst the cephalosporin compounds of the formula (I) according to this invention, the compound in which the group $R_2$ represents the group:

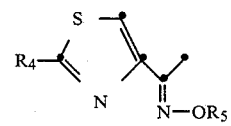

where $R_4$ and $R_5$ are as defined above, takes the syn-isomeric configuration.

Moreover, this invention also includes a solvate, particularly hydrate of the cephalosporin compound (I) within the claimed scope. Besides, this invention covers a non-toxic salt and a non-toxic ester of the cephalosporin compound (I), in particular a metabolically unstable ester thereof. By the term "non-toxic" is meant "Pharmaceutically acceptable".

As compound analogous to the compound of the general formula (I) according to this invention, there are mentioned ceftazidime and its related compounds which are shown in Japanese patent application prepublication "Kokai" No. 154786/79 specification. Ceftazidime and its related compounds are of such type in which some of the side-chain group at the 7-position of the cephem nucleus are similar to that of the new compound (I) of this invention, but they are containing such substituents at the 3-position thereof which are evidently different in nature from that of the new compound of this invention. Thus, the substituent at the 3-position of ceftazidime is pyridiniummethyl group, whereas the substituent at the 3-position of the new compound (I) of this invention is a lower alkylthio group. Besides, the abovementioned Japanese patent application prepublication does nowhere disclose that the particular compounds exemplified therein can be administered orally. In contrast, the new compound of this invention, owing to the particular combination of the specified substituents existing at the 7- and 3-positions thereof, exhibits an improved property that it can be administered not only parenterally but also orally to achieve a therapeutic effect on the bacterial infections.

Furthermore, the new compound of this invention has been found to exhibit some advantages that if shows a wider range and a higher level of antibacterial activity as well as a very much enhanced curative effect in the therapeutic treatment of bacterial infection, as compared to cephalexin, cephatriazine, cefaclor, cefroxadine and the like which are representative of orally administrable antibacterial agent of cephalosporin series, commercially available at present. For instance, some compounds which are representative of the new compound (I) of this invention have the following advantages as compared to cefroxadine. Thus, (a) As will be clear from Table 1 given below which shows antibacterial spectra of the test compounds against a variety of gram-positive and gram-negative bacteria as determined in vitro in terms of the minimum inhibitory concentraction (MIC.) of the test compounds against the various bacteria, the Example 1(b) compound, Example 2(b) compound, Example 3(b) compound and Example 4(b) compound identified later as representative examples of the new compound (I) of this invention can exhibit a wider range of the antibacterial spectrum than cefroxadine and also exhibit an effective and higher antibacterial activity against resistant strains of bacteria than cefroxadine. That is to say, the compound of this invention exhibits not only a practically effective antibacterial activity against *Staphylococcus aureus* as one of gram-positive bacteria but also exhibits a higher antibacterial activity against a wide variety of gram-negative bacteria such as *Escherichia coli, Klebsiella pneumoniae, Proteus vulgaris, Proteus mirabilis, Proteus morganii, Serratia marcescens, Shigella dysenteriae, Pseudomonas aeruginosa* etc.

(b) The new compound of this invention is highly effective in therapeutic treatment of bacterial infections in vivo even when it is administered orally. Thus, some tests were made to evaluate the curative effects of the new compound of this invention in therapeutic treatment of bacterial infections when the new compound was orally given to mice (average body weight 20 g) which had been infected with *Escherichia coli* No. 29. In these tests for therapeutic treatment of the bacterial infection, mice (three mice in each group) were inoculated intraperitoneally with *Escherichia coli* No. 29 at an inoculmn dose of $3.25 \times 10^5$ CFU/mouse and then immediately treated by oral administration of the test compound. For the subsequent 7 days, the mice were kept under observation and the number of surviving mice was counted. The test results obtained are shown in Table 2 below. For instance, the Example 6(b) compound which was tested as an example of the new compound of this invention exhibited better curative effects in therapeutic treatment of the bacterial infection in vivo.

TABLE 2

| Dosage | Example 6(b) compound of this invention | Cefroxadine (comparative) | Group of no treatment (control) |
|---|---|---|---|
| 10 mg/mouse | 3 | 3 | 0 |
| 5 mg/mouse | 3 | 3 | 0 |
| 1 mg/mouse | 3 | 0 | 0 |
| 0.1 mg/mouse | 1 | 0 | 0 |

As demonstrated by the foregoing, the new compound of the formula (I) according to this invention has some excellent properties as the antibacterial agent, so that it is a useful antibiotic which can be administered orally or parenterally for curative or preventative treatment of bacterial infections in mammalian animals, including man.

According to a further aspect of this invention, therefore, there is provided an antibacterial agent which comprises at least one of the 1-oxadethiacephalosporin compound represented by the aforesaid general formula (I), and a non-toxic salt or non-toxic ester of said compound as the active ingredient.

The non-toxic salt, that is, pharmaceutically acceptable salt of the compound of the general formula (I) includes conventional non-toxic salts (carboxylates) as formed by reaction with the carboxylic group present in

TABLE 1

| Test Organisms | Example 1(b) compound of this invention | Example 2(b) compound of this invention | Example 3(b) compound of this invention | Example 4(b) compound of this invention | Example 6(b) compound of this invention | Cefroxadine (comparative) |
|---|---|---|---|---|---|---|
| *Staphylococcus aureus* Smith | 0.20 | 0.10 | 0.39 | 3.13 | 3.13 | 1.56 |
| *Staphylococcus aureus* 209P JC-1 | 0.20 | 0.05 | 0.20 | 1.56 | 1.56 | 1.56 |
| *Escherichia coli* NIHJ JC-2 | 6.25 | 6.25 | 0.78 | 0.78 | 0.78 | 3.13 |
| *Klebsiella pneumoniae* PCI 602 | 1.56 | 1.56 | 0.78 | 0.39 | 0.10 | 3.13 |
| *Proteus mirabilis* GN 79 | 25 | 25 | 6.25 | 1.56 | 0.39 | 50 |
| *Salmonella typhimurium* LT-2 | 1.56 | 1.56 | 0.78 | 0.20 | 0.05 | 6.25 |
| *Proteus vulgaris* GN 76 | >100 | >100 | 50 | 50 | >100 | >100 |
| *Proteus rettgeri* GN 624 | >100 | >100 | 3.13 | 1.56 | 3.13 | >100 |
| *Serratia marcescens* No. 2 | >100 | >100 | 3.13 | 0.39 | 0.78 | 100 | the compound, particularly salts with inorganic bases, for example, alkali metal salts such as sodium salt and potassium salt; alkaline earth metal salts such as calcium salt, magnesium salt and zinc salt; and addition-salts with such basic amino acids as lysine, arginine, ornithine and histidine, as well as addition-salt with organic amine salt or other basic salts which usually will form a salt with cephalosporin.

Other non-toxic salts of the compound (I) of this invention include those which may be formed by adding the amino group or other basic group of said compound an inorganic acid such as hydrochloric, hydrobromic, sulfuric, nitric or phosphoric acid, an organic carboxylic or sulfonic acid such as trifluoroacetic, benzenesulfonic, methanesulfonic, maleic, tartaric or p-toluenesulfonic acid; or an acidic amino acid such as aspartic or glutamic acid, and further they may include intermolecular or intramolecular salts.

The non-toxic esters of the compound (I) of this invention are those esters of the carboxyl group present in said compound with pharmaceutically acceptable ester-forming groups. Among these are preferred metabolically unstable ester, which carry an ester-forming group cleavable upon hydrolysis in vivo. Examples of such ester-forming group include aromatic groups such as acetoxymethyl, pivaloyloxymethyl, α-ethoxycarbonyloxyethyl, phthalidyl and phenyl groups.

For use as antibacterial agent, the compound of this invention may be given orally or parenterally to adults at a unit of 50–1500 mg and preferably of 100–1000 mg four to six times per day when it is administered for therapeutic treatment of bacterial infections in man. The antibacterial agent according to this invention may usually be composed of the compound of this invention in association with a solid or liquid excipient, and it may be formulated into solid preparations such as tablets, capsules, powder and pre-treated powder, or into liquid preparations such as injectable solution or suspension and syrup. Solid or liquid excipient used for this purpose may be any one known in this field of the art. As stated above, the preparations so formed may preferably contain the compound of this invention at an amount required for the unit dosage of the compound for adult indicated above.

The new 1-oxadethiacephalosporin compound of the formula (I) according to this invention may be produced, for example, by any of the following processes (1) and (2).

Process (1)

1-Oxadethia-3-alkylthio-7-amino-cephem compound of the formula:

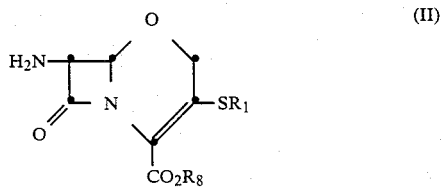

in which $R_1$ is as defined above and $R_8$ represents a hydrogen atom or a known carboxyl-protecting group, is reacted with a thienyl compound of the formula:

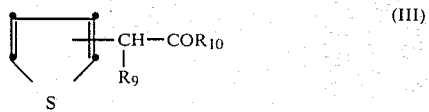

wherein $R_9$ represents a hydrogen atom or an optionally protected carboxyl group and $-COR_{10}$ represents a carboxyl group or a reactive derivative thereof to effect the acylation reaction on the 7-amino group of the compound (II), and the carboxyl-protecting group ($R_8$, etc.) is then removed optionally from the resulting 7-N-acylated product to give the desired compound of the formula (I).

Process (2)

1-Oxadethia-3-alkylthio-7-amino-cephem compound of the above formula (II) is reacted with a thisazolyl compound of the formula:

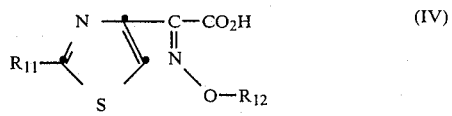

wherein $R_{11}$ represents a hdyrogen atom or an optionally protected amino group and $R_{12}$ represents an alkyl group of 1 to 4 carbon atoms or an optionally protected carboxylalkyl group, in the syn-isomeric configuration or a reactive derivative of the carboxyl group of the compound (IV) to effect the acylation reaction of the 7-amino group of the compound (II), and the carboxyl- and amino-proctecting groups are removed, if desired, from the resulting 7-N-acylated product to give the final compound of the formula (I).

The above process (1) or (2) may be carried out by employing the conventional reaction known per se in synthesis of an amide. The carboxyl-protecting groups which may be used to protect the carboxyl group of the compounds of the formulae (II), (III) or (IV) include p-nitrobenzyl, diphenylmethyl, tertbutyl, trimethylsilyl, bisdimethylsilyl, trimethoxysilyl, bisdimethoxysilyl group and the like. Removal of the carboxyl-protecting group from the acylation product may be carried out in a conventional manner known to remove the carboxyl-protecting group. Appropriate reactive derivatives of the carboxyl group of the compound (III) or (IV) may include an acid halide, an acid anhydride, an active amide, an active ester and the like. As preferred reactive derivatives of the carboxyl group, there may be mentined a derivative of Vilsmeier reagent, an acid chloride, an acid bromide, a mixed acid anhydride of substituted phosphoric acids such as dialkylphosphoric acid, phenylphosphoric acid, diphenylphosphoric acid, dibenzylphosphoric acid and halogenated phosphoric acid, a mixed acid anhydride such as mixed acid anhydride of aromatic carboxylic acids and the like, a symmetrical acid anhydride, an active amide with an imino group-containing heterocyclic compound such as imidazole, 4-substituted imidazole, dimethylpyrazole, triazole, tetrazole and the like, an active ester with an N-hydroxy compound such as N,N-dimethylhydroxyamine, 1-hydroxy-2(H)-pyridone, N-hydroxysuccinimide, N-hydroxyphthalimide, 1-hydroxybenzotriazole, 1-hydroxy-6-chlorobenzotriazole and the like.

Acylation of the 7-amino group of the compound (II) with the acid compound (III) and (IV) may preferably be carried out in the presence of a condensing agent, for example, a carbodiimide such as N,N'-dicyclohexylcarbodiimide or N-ethyl-N'-γ-diemthylaminopropylcarbodiimide; a carbonyl compound such as carbonyldiimidazole; or an isoxazolium salt such as N-ethyl-5-phenylisoxazolium perchlorate, which is known as a dehydrating agent.

The acylation reaction using the compound (III) or (IV) in the form of a free acid or its reactive derivative to provide an amide is preferably conducted in an anhydrous reaction medium such as methylene chloride, tetrahydrofuran, dimethylformamide or acetonitrile. If desired, the acylation reaction is performed in the presence of a catalyst such as 4-dimethylaminopyridine. Further, a known amino-protecting group which is usually used in the conventional synthesis of penicillin or cephalosporin compounds may be used to protect the amino group of the thiazolyl compound (IV), and such the known amino-protecting group may be removed from the protected amino group of the acylation product subsequent to the acylation reaction. Typical example of the amino-protecting groups which may be used includes trityl group, an aralkyloxycarbonyl group such as benzyloxycarbonyl and p-methoxy-benzyloxycarbonyl; an alkoxycarbonyl group such as trichloroethoxycarbonyl and t-butoxycarbonyl; an alkanoyl group such as chloroacetyl, bromoacetyl, trifluoroacetyl and formyl; phthaloyl; benzoyl group substituted with a halogen, nitro or lower alkyl or 1 to 4 carbon atoms and the like.

In case the compounds of the formula (I) in which $R_2$ represents a group of the formula

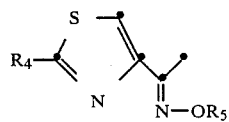

where $R_4$ and $R_5$ are as defined above, according to this invention is obtained as a mixture of isomers, its syn-isomer may be isolate from the reaction mixture in a conventional manner, e.g. by crystallization or chromatography.

The thiazolyl compound of the above formula (IV) employed as one starting mateial in the production of the desired compound (I) may be prepared according to the conventional method as disclosed in Japanese Patent Prepublication Nos. 85394/82 and 154786/79. The 1-oxadethiacephem compound of the above formula (II) employed as the other starting material for the production of the desired compound (I) may be prepared either starting with 1-oxa-1-dethia-3-hydroxycephalosporin compound of the formula

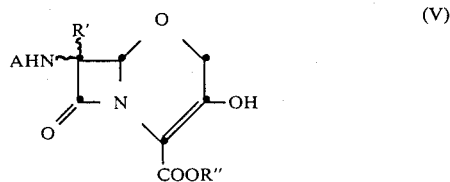

wherein A represents an acyl group, R' is a hydrogen atom or methoxy group, and R" represents a carboxyl-protecting group, which was produced according to the prior art method as disclosed in our copending Japanese Patent Application No. 198466/81 specification or starting with 1-oxa-1-dethia-3-hydroxy-3-cephem compound of the formula

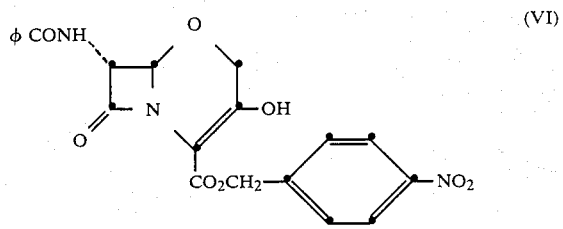

wherein φ represents a phenyl group, as disclosed in the article "Heterocycles" 18, 20–209 (1982) and with reference to the procedure of Reference Example mentioned below.

This invention is now illustrated with reference to the following Examples.

EXAMPLE 1

(a) Synthesis of diphenylmethyl 7-(2-thienylacetamido)-1-oxa-1-dethia-3-methylthio-3-cephem-4carboxylate of the formula:

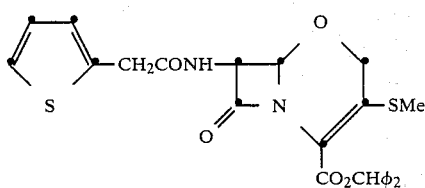

where Me represents methyl group and φ is phenyl group.

43.5 Mg (0.11 mmole) of diphenylmethyl 7-amino-1-oxa-1-dethia-3-methylthio-3-cephem-4-carboxylate was taken up into 0.6 ml of ethyl acetate. To this solution were added 12 μl of pyridine and 21 mg (0.13 mmole) of 2-thienyl acetylchloride under ice-cooling and the resultant mixture was subjected to the acylation reaction for 30 minutes.

After completion of the reaction, the reaction solution was admixed with 5 ml of ethyl acetate, washed twice with 3 ml of water, dried over magnesium sulphate, and then distilled under reduced pressure to remove the solvent. The residue so formed was chromatographed on silica gel developed with a mixed solvent of benzene-ethyl acetate (5:1 by volume) as eluent for isolation of the desired product to given 40 mg (Yield 46%) of the titled compound.

NMR,δ(CDCl$_3$): 2.2 (3H, s), 3.85 (2H,s), 4.5 (2H, s), 5.00 (1H d, J=4), 5.75 (1H dd, J=4.8), 6.4 (1H d, J=8), 6.6–7.9 (13H, m).

(b) Synthesis of 7-(2-thienylacetamido)-1-oxa-1-dethia-3-methylthio-3-cephem-4-carboxylic acid of the formula:

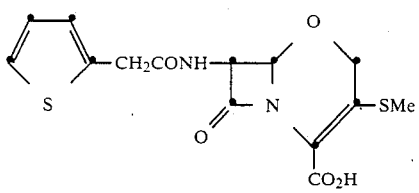

28 Mg (0.054 mmole) of the compound obtained in the preceding step (a) was admixed with 84 μl of anisole and then with 280 μl of trifluoroacetic acid under ice-cooling, and the resultant solution was subjected to the deprotection reaction for 10 minutes. After completion of the reaction, the reaction solution was distilled under reduced pressure to remove trifluoroacetic acid and the resultant residue was treated with isopropyl ether to provide a solid precipitate which was then dried to afford 13 mg (Yield 68%) of the titled compound.

NMR,δ (CD$_3$COCD$_3$): 2.2 (3H, s), 3.9 (2H, s), 4.75 (2H, s), 5.15 (1H d, J=4), 5.6 (1H dd, J=4.8), 6.9–7.4 (4H, m).

EXAMPLE 2

(a) Synthesis of diphenylmethyl 7-(3-thienylacetamido)-1-oxa-1-dethia-3-methylthio-3-cephem-4-carboxylate of the formula:

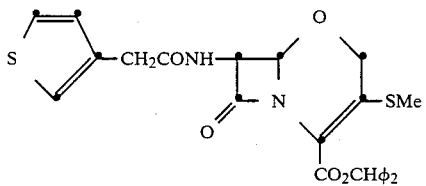

33 Mg (0.984 mmole) of diphenylmethyl 7-amino-1-oxa-1-dethia-3-methylthio-3-cephem-4-carboxylate was dissolved in 1.0 ml of methylene chloride. To this solution were added 13.1 mg (0.092 mmole) of 3-thienylacetic acid and then 19.6 mg (0.095 mmole) of dicyclohexylcarbodiimide under ice-cooling, and the resultant mixture was subjected to the acylation reaction for 3 hours.

After completion of the reaction, the reaction solution was filtered to remove the precipitate formed, distilled under reduced pressure to remove the solvent and chromatographed on silica gel developed with a mixed solvent of benzene-ethyl acetate (5:1 by volume) to give 33 mg (Yield 77%) of the titled compound.

NMR, δ (CDCl$_3$): 2.3 (3H, s), 3.70 (2H, s), 4.5 (2H, s), 5.00 (1H, d, J=4), 5.75 (1H, dd, J=4.8), 6.6–7.9 (13H, m).

(b) Synthesis of 7-(3-thienylacetamido)-1-oxa-1-dethia-3-methylthio-3-cephem-4-carboxylic acid of the formula

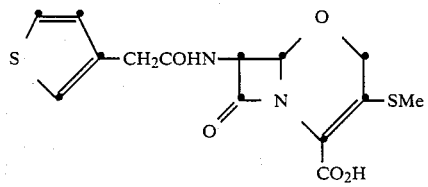

33 Mg (0.063 mmole) of the compound obtained in the preceding step (a) was admixed with 100 μl of anis-ole and then with 330 μl of trifluoroacetic acid under ice-cooling, and the resultant solution was subjected to the deprotection reaction for 10 minutes.

On completion of the reaction, the reaction solution was distilled under reduced pressure to remove trifluoroacetic acid, and the resultant residue was treated with isopropyl ether to provide a solid precipitate which was finally dried to give 15 mg (Yield 67%) of the titled compound.

NMR, δ (CD$_3$COCD$_3$): 2.35 (3H, s), 3.70 (2H, s), 4.75 (2H, s), 5.15 (1H, d, J=4), 5.60 (1H, dd, J=4.8), 7.05–7.80 (4H, m).

EXAMPLE 3

(a) Synthesis of diphenylmethyl 7-[2-(-b 2-thienyl)-2-diphenylmethoxycarbonylacetamido]-1-oxa-1-dethia-3-methylthio-3-cephem-4-carboxylate of the formula:

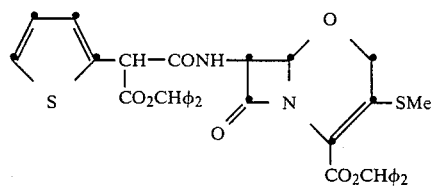

27 Mg (0.07 mmole) of diphenylmethyl 7-amino-1-oxa-1-dethia-3-methylthio-3-cephem-4-carboxylate was dissolved in 0.8 ml of methylene chloride. To this solution were added 25 mg (0.07 mmole) of monodiphenylmethyl 2-thienylmalonate and then 16.3 mg (0.08 mmole) of dicyclohexylcarbodiimide under ice-cooling and the resultant mixture was subjected to the acylation reaction overnight under ice-cooling.

On completion of the reaction, the reaction solution was filtered to remove the precipitate formed, distilled under reduced pressure to eliminate the solvent therefrom and then chromatographed on silica gel developed with a mixed solvent of benzene-ethyl acetate (15:1 by volume) as eluent for isolation of the desired product to give 40 mg (Yield 77%) of the titled compound.

NMR, δ (CDCl$_3$): 2.10 (3H, s), 4.35 (2H, bs), 4.85 (1H, d, J=4), 4.90 (1H, s), 5.5 (1H, dd, J=4.8), 6.75–7.5 (16H).

(b) Synthesis of 7-[2-(2-thienyl)-2-carboxyacetamido]-1-oxa-1-dethia-3-methylthio-3-cephem-4-carboxylic acid of the formula

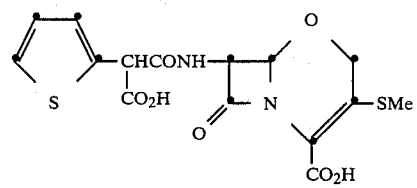

60 Mg (0.082 mmole) of the compound obtained in the preceding step (a) of this Example was admixed with 180 μl of anisole and then with 600 μl of trifluoroacetic acid under ice-cooling, and the resultant solution was subjected to the deprotection reaction for 10 minutes. On completion of the reaction, the reaction solution was distilled under reduced pressure to remove trifluoroacetic acid, and the resultant residue was treated with isopropyl ether to provide a solid precipitate which was finally dried to afford 21 mg (Yield 64%) of the titled compound.

NMR, δ (CD₃COCD₃): 2.30, 2.33 (3H, s), 4.25, 4.30 (2H, s), 5.15 (1H, s), 5.25 (1H, d, J=4), 5.65 (1H, d, J=4.8), 6.9–7.5 (3H, m), 8.20 (1H, d, J=8).

EXAMPLE 4

(a) Synthesis of diphenylmethyl 7-[2-(3-thienyl)-2-diphenylmethoxycarbonylacetamido]-1oxa-1-dethia-3-methylthio-3-cephem-4-carboxylate of the formula:

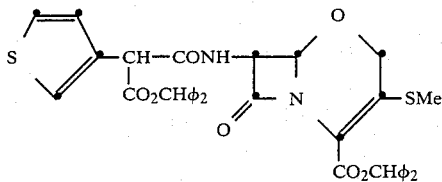

27 Mg (0.07 mmole) of diphenylmethyl 7-amino-1-oxa-1-dethia-3-methylthio-3-cephem-4-carboxylate was taken up in 0.8 ml of methylene chloride. To this solution were added 25 mg (0.07 mmole) of monodiphenylmethyl 3-thienylmalonate of the formula:

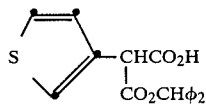

and subsequently 16.3 mg (0.08 mmole) of dicyclohexylcarbodiimide under ice-cooling, and the resultant mixture was subjected to the acylation reaction overnight.

On completion of the rection, the reaction solution was filtered to remove the precipitate formed, distilled under reduced pressure to eliminate the solvent therefrom and then chromatographed on silica gel developed with a mixed solvent of benzene-ethyl acetate (15:1 by volume) as eluent for isolation of the desired product to give 46 mg (Yield 88%) of the titled compound.

NMR, δ (CDCl₃): 2.20 (3H, s), 4.50 (2H, bs), 4.85–5.00 (2H), 5.65 (1H, dd, J=4.8), 6.9 (1H, s), 7.0–7.5 (24H). (b) Synthesis of 7-[2-(3-thienyl)-2-carboxyacetamido]-1-oxa-1-dethia-3-methylthio-3-cephem-4-carboxylic acid of the formula:

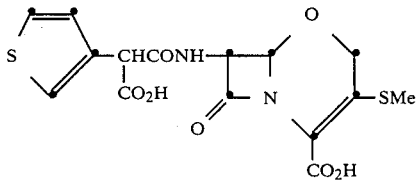

46 Mg (0.063 mmole) of the compound obtained in the preceding step (a) of this Example was admixed with 140 μl of anisole and subsequently with 460 μl of trifluoroacetic acid under ice-cooling, and the resultant solution was subjected to the deprotection reaction for 10 minutes. On completion of the reaction, the reaction solution was distilled under reduced pressure to remove trifluoroacetic acid, and the resultant residue was treated with isopropyl ether, giving a solid precipitate which was finally dried to afford 17 mg (Yield 68%) of the titled compound.

NMR, δ(CD₃COCD₃): 2.25, 2.30 (3H, s), 4.70, 4.75 (2H, s), 4.9 (1H, s), 5.13, 5.18 (1H, d, J=4), 5.55 (1H, dd, J=4.8), 7.10–7.50 (3H, m), 8.1 (1H, d, J=8).

EXAMPLE 5

(a) Synthesis of diphenylmethyl 7-[2-(3-thienyl)-2-phenoxycarbonylacetamido]-1-oxa-1-dethia-3-methylthio-3-cephem-4-carboxylate:

63 Mg (0.16 mmole) of diphenylmethyl 7-amino-1-oxa-1-dethia-3-methylthio-3-cephem-4-carboxylate was dissolved in 1.2 ml of methylene chloride. To this solution was added 43 mg (0.17 mmole) of monophenyl 3-thienylmalonate with stirring under ice-cooling. The resultant mixture was admixed with 24 mg (0.176 mmole) of 1-hydroxybenzotriazole and then with 36 mg (0.176 mmole) of dicyclohexylcarbodiimide, and the admixture thus formed was subjected to the acylation reaction under ice-cooling for one hour and at ambient temperature for further one hour. On completion of the reaction, the reaction solution was filtered to remove the insoluble matter therefrom and distilled under reduced pressure to eliminate the methylene chloride as solvent. The resulting residue was taken up in 5 ml of ethyl acetate, and the solution thus formed was washed with water (2 ml), aqueous saturated sodium bicarbonate solution (2 ml) and with water (2 ml×3), and dried over anhydrous magnesium sulphate. The dried solution was chromatographed on silica gel developed with a mixed solvent of benzene-ethyl acetate (10:1 by volume) as eluent for isolation of the desired product to give 62 mg (Yield 60%) of the titled compound.

NMR, δ(CDCl₃): 2.15, 2.18 (3H, s), 4.45, 4.50 (2H, d), 4.95 (1H, s), 5.00 (1H, d), 5.20, 5.23 (1H, dd), 6.85 (1H, s). 7.0–7.7 (18H, m).

(b) Synthesis of 7-[2-(3-thienyl)-2-phenoxycarbonylacetamido]-1-oxa-1-dethia-3-methylthio-3-cephem-4-carboxylic acid of the formula:

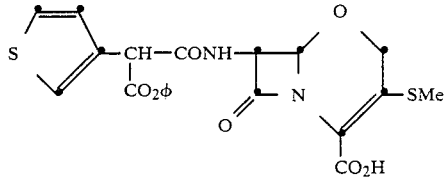

100 Mg (0.156 mmole) of the product obtained in the preceding step (a) of this Example was dissolved in 300 μl of anisole and then with 1.0 ml of trifluoroacetic acid under ice-cooling. The resultant solution was subjected to the deprotection reaction for 10 minutes and distilled under reduced pressure to remove the trifluoroacetic acid. The resulting residue was treated with isopropyl ether to provide a solid precipitate which was finally dried to give 56 mg (Yield 87.5%) of the titled compound.

NMR, δ(CD₃COCD₃): 2.35 (3H), 4.75 (2H), 5.25 (2H), 5.65 (1H), 7.0–7.7 (8H), 8.15 (1H).

EXAMPLE 6

(a) Synthesis of diphenylmethyl 7-[2-(2-tritylamino-4-thiazolyl)-2-methoxyiminoacetamido]-1-oxa-1-dethia-3-methylthio-3-cephem-4-carboxylate (syn-isomer) of the formula:

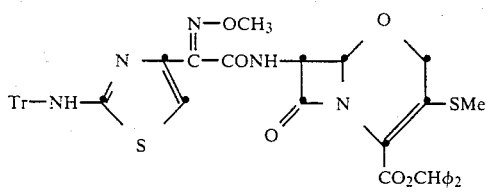

where the symbol Tr represents a trityl group.

93 Mg (0.235 mmole) of diphenylmethyl 7-amino-1-oxa-1-dethia-3-methylthio-3-cephem-4-carboxylate was dissolved in 2.8 ml of methylene chloride. To this solution was added 106 mg (0.24 mmole) of 2-(2-tritylamino-4-thiazolyl)-2-methoxyiminoacetic acid (syn-isomer) of the formula:

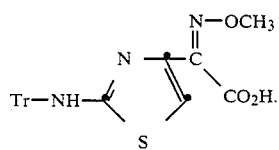

The resultant mixture was admixed with 78 μl of pyridine and 40 μl of phosphorus oxychloride under ice-cooling, and the admixture so formed was subjected to the acylation reaction for 30 minutes. On completion of the reaction, the reaction solution was admixed with 10 ml of dichloromethane and 5 ml of water to give a two-phase system, and the separated solution was washed with aqueous sodium bicarbonate solution and with 5 ml of water, dried over anhydrous magnesium sulphate and finally distilled to remove the solvent therefrom. The resultant residue was chromatographed on silica gel developed with a mixed solvent of benzene-ethyl acetate (5:1 by volume) as eluent for isolation of the desired product to give 165 mg (Yield 85.6%) of the titled compound.

NMR, δ(CDCl$_3$): 2.25 (3H, s), 4.05 (3H, s), 4.60 (2H, d), 5.07 (1H, d, J=4), 5.77 (1H, dd, J=4, 8), 6.7 (1H, d, J=8), 6.85 (1H, s), 7.1–7.7 (25H).

(b) Synthesis of 7-[2-(2-amino-4-thiazolyl)-2-methoxyiminoacetamido]-1-oxa-1-dethia-3-methylthio-3-cephem-4-carboxylic acid trifluoroacetate (syn-isomer) of the formula:

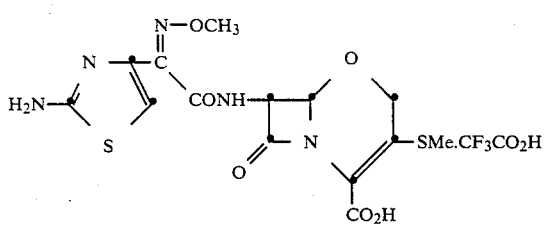

165 Mg (0.2 mmole) of the product, (syn-isomer) obtained in the preceding step (a) of this Example was taken up in 500 μl of anisole. To this solution was added 1.65 ml of trifluoroacetic acid, and the resultant mixture was subjected to the deprotection reaction for 30 minutes. On completion of the reaction, the reaction solution was treated with isopropyl ether to obtain a precipitate which was dried to give 73 mg (Yield 70.6%) of the titled compound.

NMR, δ(CD$_3$SOCD$_3$): 2.3 (3H, s), 3.85 (3H, s), 4.73 (2H, d), 5.15 (1H, d, J=4), 5.48 (1H, dd, J=4, 8), 6.75 (1H, s), 9.33 (1H, d, J=8).

EXAMPLE 7

(a) Synthesis of diphenylmethyl 7-[2-(2-tritylamino-4-thiazolyl)-2-ethoxyiminoacetamido]-1-oxa-1-dethia-3-methylthio-3-cephem-4-carboxylate (syn-isomer) of the formula:

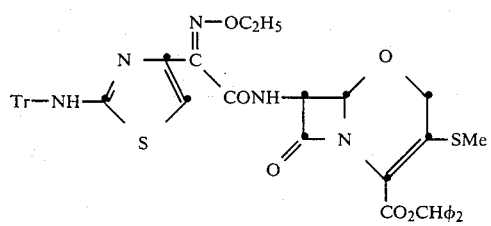

91 mg (0.23 mmole) of diphenylmethyl 7-amino-1-oxa-1-dethia-3-methylthio-3-cephem-4-carboxylate was dissolved in 2.7 ml of methylene chloride. To this solution were added 116 mg (0.25 mmole) of 2-(2-tritylamino-4-thiazolyl)-2-ethoxyiminoacetic acid (syn-isomer) and 78 μl of pyridine and 40 μl (0.26 mmole) of phosphorus oxychloride under ice-cooling, and the resultant mixture was subjected to the acylation reaction for 30 minutes. On completion of the reaction, the reaction solution was admixed with 10 ml of methylene chloride and 5 ml of water to separate it into a two-phase system. The resulting organic solution was washed with aqueous sodium bicarbonate solution and with water (5ml×2), dried over anhydrous magnesium sulphate and distilled under reduced pressure to remove the solvent employed. The resultant residue was chromatographed on silica gel developed with a mixed solvent of benzene-ethyl acetate (5:1 by volume) as eluent for isolation of the desired product to afford 122 mg (Yield 64%) of the titled compound.

NMR, δ(CDCl$_3$): 1.25 (3H, t, J=8), 2.2 (3H, s), 3.95 (2H, l, J=8), 4.10 (2H, d), 5.00 (1H, d, J=4), 5.60 (1H, d, J=8), 6.60 (1H, s), 7.1–7.7 (25H).

(b) Synthesis of 7-[2-(2-amino-4-thiazolyl)-2-ethoxyiminoacetamido]-1-oxa-1-dethia-3-methylthio-3-cephem-4-carboxylic acid trifluoroacetate (syn-isomer) of the formula:

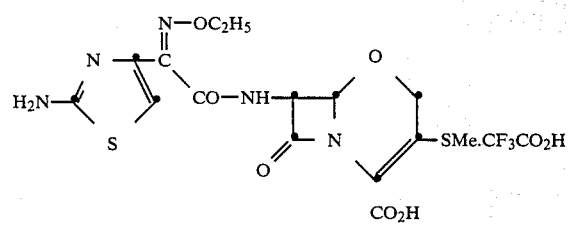

122 Mg (0.146 mmole) of the product obtained in the preceding step (a) of this Example was dissolved in 370 μl of anisole. To this solution was added 1.22 ml of trifluoroacetic acid under ice-cooling, and the resultant mixture was subjected to the deprotection reaction for 30 minutes. On completion of the reaction, the reaction solution was treated with isopropyl ether to obtain a precipitate which was dried to give 52 mg (Yield 67.5%) of the titled compound.

NMR, δ(CD₃SOCD₃): 1.15 (3H, t, J=8), 2.2 (3H, s), 4.0 (2H, q, J=8), 4.65 (2H, bs), 5.05 (1H, d, J=4), 5.40 (1H, d, J=8), 6.65 (1H, s), 9.12 (1H, d, J=8).

EXAMPLE 8

(a) Synthesis of diphenylmethyl 7-[2-(2-tritylamino-4-thiazolyl)-2-tert-butoxycarbonylmethoxyiminoacetamido]-1-oxa-1-dethia-3-methylthio-3-cephem-4-carboxylate (syn-isomer) of the formula:

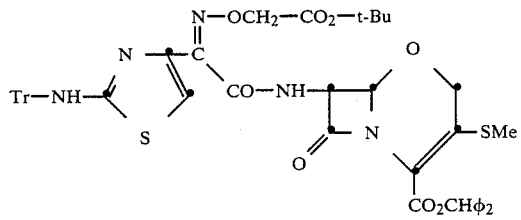

44 Mg (0.11 mmole) of diphenylmethyl 7-amino-1-oxa-1-dethia-3-methylthio-3-cephem-4-carboxylate was dissolved in 1.3 ml of methylene chloride, and the resultant solution was admixed with 60 mg (0.11 mmole) of 2-(2-tritylamino-4-thiazolyl)-2-tert-butoxycarbonylmethoxyiminoacetic acid (syn-isomer) and subsequently under ice-cooling with 36 μl of pyridine and 11.4 μl of phosphorus oxychloride. The admixture so formed was subjected to the acylation reaction for 30 minutes. After completion of the reaction, the reaction solution was admixed with 4 ml of methylene chloride and 2 ml of water to separate it into a two-phase system. The resulting organic solution was washed with aqueous sodium bicarbonate solution and with water (2 ml×2), dried over anhydrous magnesium sulphate and distilled under reduced pressure to remove the solvent employed. The resultant residue was chromatographed on silica gel developed with a mixed solvent of benzene-ethyl acetate (5:1 by volume) as eluent for isolation of the desired product to afford 50 mg (Yield 50%) of the titled compound.

NMR, δ(CDCl₃): 1.4 (9H, s), 2.20 (3H, s), 4.5 (2H, d), 4.85 (s, 2H), 5.0 (1H, d, J=4), 5.75 (1H, d, J=4, 8), 6.70 (1H, s), 6.90 (1H, s), 7.0–7.6 (25H), 8.0 (1H, d, J=8).

(b) Synthesis of 7-[2-(2-amino-4-thiazolyl)-2-carboxymethoxyiminoacetamido]-1-oxa-1-dethia-3-methylthio-3-cephem-4-carboxylic acid trifluoroacetate (syn-isomer) of the formula:

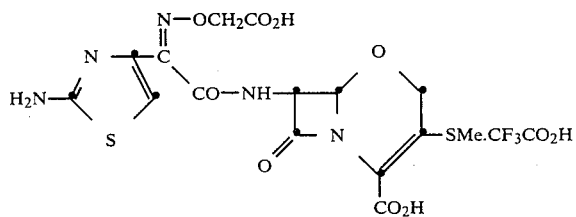

50 Mg (0.05 mmole) of the product obtained in the preceding step (a) of this Example was dissolved in 150 μl of anisole, and the resultant solution was admixed with 0.5 ml of trifluroracetic acid under ice-cooling and subjected to the deprotection reaction for 60 minutes. On completion of the reaction, the reaction solution was treated with isopropyl ether to obtain a precipitate which was then dried to afford 21 mg (Yield 66%) of the titled compound.

NMR, δ(CD₃SOCD₃): 2.25 (3H, s), 4.6 (4H), 5.15 (1H, d, J=4), 5.55 (1H, dd, J=4, 8),6.8 (1H, s), 9.2 (1H, d, J=8).

EXAMPLE 9

(a) Synthesis of diphenylmethyl 7-[2-(2-tritylamino-4-thiazolyl)-2-phenoxycarbonylmethoxyiminoacetamido]-1-oxa-1-dethia-3-methylthio-3-cephem-4-carboxylate (syn-isomer) of the formula

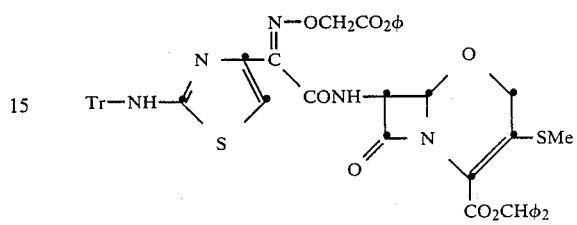

44 Mg (0.11 mmole) of diphenylmethyl 7-amino-1-oxa-1-dethia-3-methylthio-3-cephem-4-carboxylate was dissolved in 1.3 ml of methylene chloride, and the resultant solution was admixed with 62 mg (0.11 mmole) of 2-(2-tritylamino-4-thiazolyl)-2-phenoxycarbonylmethoxyiminoacetic acid (syn-isomer) and subsequently with 36 μl of pyridine and 11.4 μl of phosphorous oxychloride at 0° C. The admixture so formed was subjected to the acylation reaction for 30 minutes. On completion of the reaction, the reaction solution was admixed with 5 ml of methylene chloride and 2 ml of water to separate it into a two-phase system, and the resultant organic solution was washed with aqueous sodium bicarbonate solution and with water (2 ml×2), dried over anhydrous magnesium sulphate and distilled under reduced pressure to remove the solvent employed. The resultant residue was chromatographed on silica gel developed with a mixed solvent of benzene-ethyl acetate (5:1 by volume) as eluent for isolation of the desired product to provide 52 mg (Yield 50%) of the titled compound.

NMR, δ(CDCl₃): 2.20 (3H, s), 4.53 (2H, d), 4.8 (2H, s), 5.03 (1H, d, J=4), 5.70 (1H, d, J=4, 8), 6.78 (1H, s), 6.85 (1H, s), 7.0–7.6 (30H), 7.95 (1H, d, J=8).

(b) Synthesis of 7-[2-(2-amino-4-thiazolyl)-2-phenoxycarbonylmethoxyiminoacetamido ]-1-oxa-1-dethia-3-methylthio-3-cephem-4-carboxylic acid trifluoroacetate (syn-isomer):

52 Mg (0.055 mmole) of the product obtained in the preceding step (a) of this Example was dissolved in 150 μl of anisole, and the resultant solution was admixed with 0.5 ml of trifluoroacetic acid under ice-cooling and subjected to the deprotection reaction for 30 minutes. On completion of the reaction, the reaction solution was treated with isopropyl ether to obtain a precipitate which was then dried to provide 24 mg (Yield 66%) of the titled compound.

NMR, δ(CD₃SOCD₃): 2.30 (3H, s), 4.65 (4H), 5.15 (1H, s, J=4), 5.5 (1H, dd, J=4,8), 6.8 (1H, s), 7.25 (5H), 9.25 (1H, d, J=8).

EXAMPLE 10

(a) Synthesis of diphenylmethyl 7-[2-(2-tritylamino-4-thiazolyl)-2-tert-butoxycarbonylprop-2-oxyiminoacetamido]-1-oxa-1-dethia-3-methylthio-3-cephem-4-carboxylate (syn-isomer) of the formula:

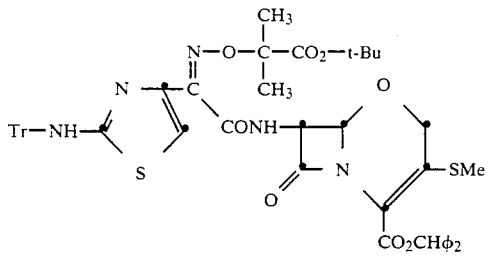

44 Mg (0.11 mmole) of diphenylmethyl 7-amino-1-oxa-1-dethia-3-methylthio-3-cephem-4-carboxylate was dissolved in 1.3 ml of methylene chloride, and the resultant solution was admixed with 63 mg (0.11 mmole) of 2-(2-tritylamino-4-thiazolyl)-2-tert-butoxycarbonyl-prop-2-oxyiminoacetic acid (syn-isomer) and subsequently with 36 μl of pyridine and 11.4 μl of phosphorus oxychloride at 0° C. The admixture so formed was subjected to the acylation reaction for 30 minutes. On completion of the reaction, the reaction solution was admixed with 5 ml of methylene chloride and 2 ml of water to separate it into a two-phase system, and the resultant organic solution was washed with aqueous sodium bicarbonate solution and with water (2 ml×2), dried over anhydrous magnesium sulphate and distilled under reduced pressure to remove the solvent employed. The resultant residue was chromatographed on silica gel developed with a mixed solvent of benzene-ethyl acetate (5:1 by volume) as eluent for isolation of the desired product to afford 52 mg (Yield 50%) of the titled compound.

NMR, δ(CDCl$_3$): 1.4 (9H, s), 1.6 (3H, s), 1.65 (3H, s), 2.2 (3H, s), 4.6 (2H, s), 5.1 (1H, d, J=4), 5.7 (1H, d, J=4, 8), 6.70 (1H, s), 6.85 (1H, s), 7.0–7.7 (25H), 7.9 (1H, d, J=8). (b) Synthesis of 7-[2-(2-amino-4-thiazolyl)-2-carboxyprop-2-oxyiminoacetamido]-1-oxa-1-dethia-3-methylthio-3-cephem-4-carboxylic acid trifluoroacetate (syn-isomer) of the formula:

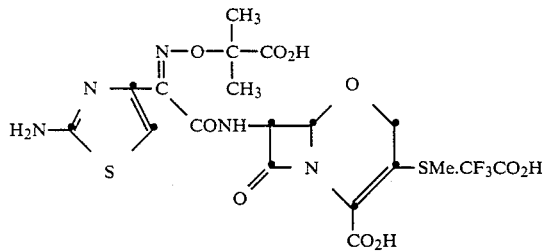

52 Mg (0.055 mmole) of the product obtained in the preceding step (a) of this Example was dissolved in 150 μl of anisole, and the resultant solution was admixed with 520 μl of trifluoroacetic acid at 0° C. and subjected to the deprotection reaction for 60 minutes. On completion of the reaction, the reaction solution was treated with isopropyl ether to obtain a precipitate which was then dried to provide 21 mg (Yield 60%) of the titled compound.

NMR, δ (Cd$_3$SOCD$_3$): 1.35 (3H, s), 1.40 (3H, s), 2.25 (3H, s), 4.65 (2H, s) 5.05 (1H, d, J=4), 5.5 (1H, dd, J=4, 8), 6.8 (1H, s), 9.3 (1H, d, J=8).

EXAMPLE 11

(a) Synthesis of diphenylmethyl 7-[2-(2-tritylamino-4-thiazolyl)-2-phenoxycarbonylprop-2-oxyiminoacetamido]-1-oxa-1-dethia-3-methylthio-3-cephem-4-carboxylate (syn-isomer) of the formula:

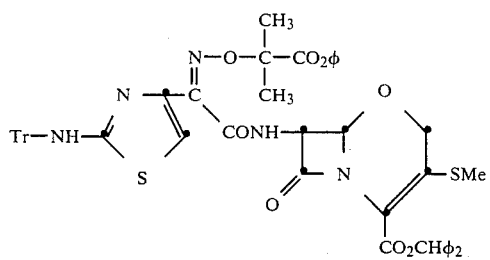

44 Mg (0.11 mmole) of diphenylmehtyl 7-amino-1-oxa-1-dethia-3-methylthio-3-cephem-4-carboxylate was dissolved in 1.3 ml of methylene chloride, and the resultant solution was admixed with 65 mg (0.11 mmole) of 2-(2-tritylamino-4-thiazolyl)-2-phenoxycarbonylprop-2-oxyiminoacetic acid (syn-isomer) and subsequently with 36 μl of pyridine and 11.4 μl (0.12 mmole) of phosphorus oxychloride at 0° C. The admixture thus formed was subjected to the acylation reaction for 30 minutes. On completion of the reaction, the reaction solution was admixed with 5 ml of methylene chloride and 2 ml of water to separate it into a two-phase system, and the resultant organic solution was washed with aqueous sodium bicarbonate solution and with water (2 ml×2), dried over anhydrous magnesium sulphate and distilled under reduced pressure to remove the solvent employed. The resultant residue was chromatographed on silica gel which was developed with a mixed solvent of benzeneethyl acetate (5:1 by weight) as eluent to provide 58 mg (Yield 55%) of the titled compound.

NMR, δ (CDCl$_3$): 1.6 (3H, s), 1.65 (3H, s), 2.20 (3H, s), 4.8 (2H, s) 5.05 (1H, d, J=4), 5.70 (1H, d, J=4, 8), 6.80 (1H, s), 6.90 (1H, s), 7.0–7.6 (30H), 8.00 (1H, d, J=8).

(b) Synthesis of 7-[2-(2-amino-4-thiazolyl)-2-phenoxycarbonylprop-3-oxyiminoacetamido]-1-oxa-1-dethia-3-methylthio-3-cephem-4-carboxylic acid trifluoroacetate (syn-isomer):

55 Mg (0.057 mmole) of the product obtained in the preceding step (a) of this Example was dissolved in 165 μl of anisole, and the resulting solution was admixed with 550 μl of trifluoroacetic acid at 0° C. and then subjected to the deprotection reaction for 30 minutes. On completion of the reaction, the reaction solution was treated with isopropyl ether to precipitate a solid substance which was then dried to provide 23 mg (Yield 60%) of the titled compound.

NMR, δ (CD$_3$SOCD$_3$): 1,35 (3H, s), 1.40 (3H, s), 2.30 (3H, s), 5.15 (1H, s, J=4), 5.6 (1H, dd, J=4.8), 6.8 (1H, s), 7.25 (5H), 9.25 (1H, d, J=8).

REFERENCE EXAMPLE (a) Synthesis of p-nitrobenzyl 7-α-benzoylamino-1-oxa-1-dethia-3-methylthio-3-cephem-4-carboxylate of the formula:

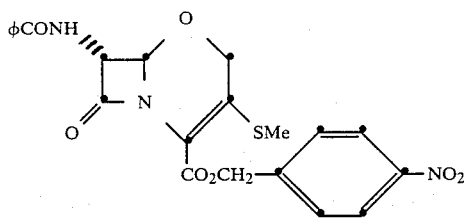

wherein the symbol φ represents a phenyl and Me methyl group.

440 Mg (1 mmole) of p-nitrobenzyl 7-α-benzoylamido-1-oxa-1-dethia-3-hydroxy-3-cephem-4-carboxylate was dissolved in 44 ml of ethyl acetate and the resultant solution was cooled to −30° C. To this solution were added 193 μl of diisopropylethylamine and then 10 minutes later 77 μl (1 mmole) of methanesulfonyl chloride, and the resultant mixture was subjected to the sulfonylation reaction for 10 minutes.

On completion of the reaction, the reaction solution was admixed with 386 μl of diisopropylethylamine and 0.8 ml of solution of 30% methylmercaptan in methanol, followed by the reaction at 5° C. for 2 hours.

On completion of said reaction, the reaction solution was washed with 10 ml of water, with 10 ml of 1N HCl and with 10 ml of water, dried over anhydrous magnesium sulfate and distilled under reduced pressure to remove the solvent employed. The resultant residue was chromatographed on silica gel developed with a mixed solvent of benzene-ethyl acetate (5:1 by volume) as eluent to provide 120 mg of the titled compound. Mass spectrum (M/e): 469 (M+).

NMR, δ (CD$_3$COCD$_3$): 3.4 (3H, s) 4.7 (2H, s), 5.0 (1H, dd, J=1, 8), 5.45 (1 H, d, J=1), 5.5 (2H, s), 7.4–8.3 (9H), 8.65 (1H, d, J=8).

(b) Synthesis of diphenylmethyl 7-α-benzoylamino-1-oxa-1-dethia-3-methylthio-3-cephem-4-carboxylate of the formula:

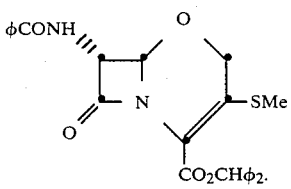

234 Mg of the product obtained in the preceding step (a) was dissolved in 70 ml of a mixed solvent of ethanol and water (90:10 by volume) and the resulting solution was admixed with 23 mg of 10% Pd on carbon and hydrogenolyzed with a stream of hydrogen to effect the deprotection reaction at 4-carboxylate at ambient temperature for 1 hour. Thereafter, the reaction solution was filtered to remove the catalyst employed and concentrated to a small volume.

The concentrated solution was admixed with a solution of diphenyldiazomethane in methylene chloride to effect the esterification reaction of 4-carboxyl group and concentrated to a small volume for removal of the solvent and then chromatographed on silica gel developed with a mixed solvent of benzene-ethyl acetate (3:1 by volume) as eluent to afford 240 mg of the titled compound.

NMR, δ (CDCl$_3$): 2.3 (3H, s), 4.5 (2H, AB q), 4.9 (1H, d, J=1), 5.0 (1H, dd, J=1, 8), 6.9 (1H, s), 7.0–7.9 (16H).

(c) Synthesis of diphenylmethyl 7-α-amino-1-oxa-1-dethia-3-methylthio-3-cephem-4-carboxylate of the formula:

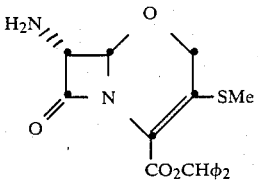

500 Mg (1 mmole) of the product obtained in the preceding step (b) of this example was taken up in 6 ml of methylene chloride.

To a suspension of 416 mg (2 mmole) of phosphorus pentachloride in 4 ml of methylene chloride was added 240 μl of pyridine at 0° C., and the resultant mixture was subjected to the reaction at ambient temperature for 30 minutes. On completion of the reaction, the solution of β-lactam in methylene chloride was added dropwise to the reaction solution, followed by the reaction for 1 hour.

On completion of the reaction, the resultant solution was cooled to −30° C. and admixed with 5 ml of methanol to effect the reaction at 2 to 3° C. for 30 minutes. Thereafter, the reaction solution was again cooled to −30° C. and admixed with 5 ml of water to effect the reaction at 2 to 3° C. for 30 minutes.

Then the whole mixture was concentrated, admixed with 20 ml of ethyl acetate and adjusted to pH 7.0 by addition of sodium bicarbonate.

The resulting solution was washed with 5 ml of water, dried over anhydrous magnesium sulphate and distilled under reduced pressure to remove the solvent therefrom. The residue obtained was chromatographed on silica gel developed with a mixed solvent of benzene-ethyl acetate (1:1 by volume) as eluent for adsorption of the desired product to give 280 mg of the titled compound.

NMR, δ(CDCl$_3$): 2.2 (3H, s), 4.0 (1H, s), 4.5 (2H, d), 4.65 (1H, s), 6.95 (1H, s), 7.0–8.0 (11H).

(d) Synthesis of diphenylmethyl 7-α-(3,5-di-tert-butyl-4-hydroxybenzylidenamino)-1-oxa-1-dethia-3-methylthio-3-cephem-4-carboxylate of the formula

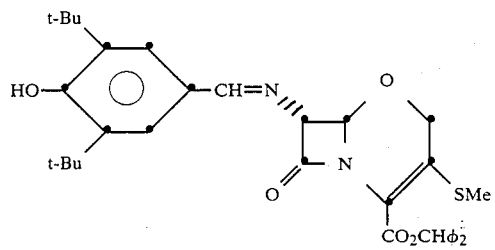

160 Mg (0.4 mmole) of the product obtained in the preceding step (c) of this Example was dissolved in 64 ml of benzene, and the resultant solution was admixed with 103 mg of 3,5-di-tert-butyl-4-hydroxybenzaldehyde, heated under reflux and then concentrated to a small volume to give 260 mg of the titled compound.

NMR, δ(CDCl₃): 1.50 (18H, s), 2.3 (3H, s), 4.65 (2H, d), 4.75 (1H, s), 5.15 (1H, s), 5.6 (9H, s), 6.95 (1H, s), 7.2-8.0 (13H), 8.45 (1H, d).

(e) Synthesis of diphenylmethyl 7-β-(3,5-di-tert-butyl-4-hydroxybenzylidenamino)-1-oxa-1-dethia-3-methylthio-3-cephem-4-carboxylate of the formula:

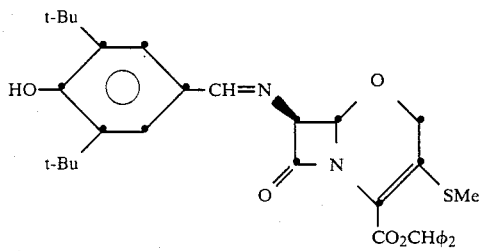

260 Mg (0.4 mmole) of the product obtained in the preceding step (d) of this Example was dissolved in 5.2 ml of methylene chloride, and the resultant solution was admixed with 160 mg of magnesium sulphate and 154 mg of nickel peroxide at 0° C., followed by the reaction for 10 minutes.

After completion of the reaction, the reaction admixture was filtered with a filter aid to remove an insoluble matter and admixed with 16 mg (0.11 mmole) of tetraethylammonium borohydride under ice-cooling, followed by the reaction for 30 minutes.

On completion of the reaction, the resultant reaction solution was adjusted to pH 6.5 by addition of 1N HCl, washed twice with 10 ml of water, dried over anhydrous magnesium sulphate and concentrated to a small volume. Thus, there was afforded 286 mg of the titled compound. This compound was used as such in the subsequent step, i.e. without purification thereof.

(f) Synthesis of diphenylmethyl 7-amino-1oxa-1-dethia-3-methylthio-3-cephem-4-carboxylate of the formula:

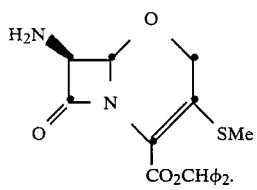

286 Mg of the product obtained in the preceding step (e) was dissolved in 4.8 ml of methylene chloride, and to this solution was dropwise added 5.3 ml of a solution of 133 mg of Girard reagent T in methanol under ice-cooling. 30 Minutes later, the reaction solution was admixed with 15 ml of ethyl acetate, washed with water (10 ml ×2), dried over anhydrous magnesium sulphate and then distilled under reduced pressure to remove the solvent therefrom. The resulting residue was hromatographed on silica gel developed with a mixed solvent of benzene-ethyl acetate (1:1 by volume) as eluent to afford 93 mg of the titled compound.

NMR, δ(CDCl₃): 2.3 (3H, s), 4.5 (1H, d, J=8), 4.6 (2H, d), 5.0 (2H, d, J=8), 6.9 (1H, s), 7.1–7.6 (10H).

What is claimed is:

1. A compound of the formula:

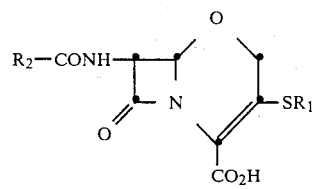

wherein $R_1$ represents an alkyl group of 1 to 4 carbon atoms and $R_2$ is a group of the formula:

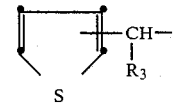

in which $R_3$ is a hydrogen atom or carboxyl group, or a group of the formula:

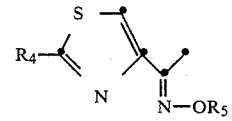

in which $R_4$ is a hydrogen atom or amino group, and $R_5$ represents an alkyl group of 1 to 4 carbon atoms or a group of the formula:

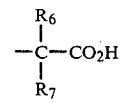

where $R_6$ and $R_7$ may be the same or different and each is a hydrogen atom or an alkyl group of 1 to 4 carbon atoms, or a non-toxic salt or non-toxic ester of said compound.

2. An antibacterial agent which comprises as the active ingredient an antibacterially effective amount of one or more of a compound of the formula:

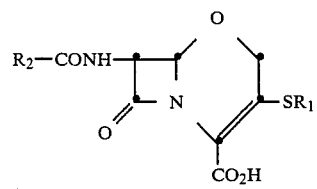

wherein $R_1$ represents an alkyl group of 1 to 4 carbon atoms and $R_2$ is a group of the formula:

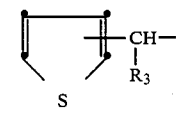

in which $R_3$ is a hydrogen atom or carboxyl group, or a group of the formula:

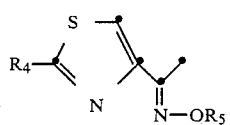
in which $R_4$ is a hydrogen atom or amino group, and $R_5$ represents an alkyl group of 1 to 4 carbon atoms or a group of the formula:
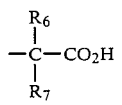
where $R_6$ and $R_7$ may be the same or different and each is a hydrogen atom or an alkyl group of 1 to 4 carbon atoms, or a non-toxic salt or non-toxic ester thereof and a solid or liquid excipient.
* * * * *